US00PP24111P2

(12) United States Plant Patent
Crook

(10) Patent No.: US PP24,111 P2
(45) Date of Patent: Dec. 24, 2013

(54) ***BEGONIA* PLANT NAMED 'BRXSI13-0'**

(50) Latin Name: *Begonia rex cultorum*
Varietal Denomination: BRXSI13-0

(76) Inventor: Gary Crook, Silverton, OR (US)

( * ) Notice: Subject to any disclaimer, the term of this patent is extended or adjusted under 35 U.S.C. 154(b) by 10 days.

(21) Appl. No.: 13/506,600

(22) Filed: Apr. 30, 2012

(51) Int. Cl.
*A01H 5/00* (2006.01)

(52) U.S. Cl.
USPC ..... Plt./343

(58) Field of Classification Search
USPC ..... Plt./343
See application file for complete search history.

*Primary Examiner* — Kent L Bell
(74) *Attorney, Agent, or Firm* — Cassandra Bright

(57) ABSTRACT

A new and distinct *Begonia rex cultorum* cultivar named 'BRXSI13-0' is disclosed, characterized by pronounced basal branching, vigorous year round growth, including the dark winter months. Plants produce small sized foliage and flexible petioles resistant to breakage. The new variety is a *Begonia*, and is normally used as an ornamental plant.

1 Drawing Sheet

Latin name of the genus and species: *Begonia rex cultorum*. Variety denomination: 'BRXSI13-0'.

BACKGROUND OF THE INVENTION

The new cultivar is a product of a planned breeding program. The new variety originated as the result of a crossing performed in 2009 of the unnamed, unpatented, proprietary seed parent variety of *Begonia rex cultorum* with the unnamed, unpatented, proprietary pollen parent, variety of *Begonia rex cultorum*. The new variety was discovered by the inventor, Gary Crook, a citizen of the United States, at a commercial greenhouse in Scotts Mills, Oreg. during 2010, among a planting of seedlings resulting from the previously mentioned crossing.

Asexual reproduction of the new cultivar 'BRXSI13-0' was first performed in Scotts Mills, Oreg. in 2010, by vegetative leaf cuttings. 'BRXSI13-0' has since produced several generations by vegetative leaf cuttings and has shown that the unique features of this cultivar are stable and reproduced true to type.

SUMMARY OF THE INVENTION

The cultivar 'BRXSI13-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BRXSI13-0.' These characteristics in combination distinguish 'BRXSI13-0' as a new and distinct *Begonia rex cultorum* cultivar:

1. Pronounced basal branching
2. Vigorous, year round growth.
3. Flexible petioles, resisting breakage.
4. Small sized leaf, for this category of Rex *Begonia*.
5. Vigorous growth at lower temperatures.

PARENT COMPARISON

Plants of the new cultivar 'BRXSI13-0' are similar to plants of the unnamed seed parent variety, in most horticultural characteristics. However, plants of the new cultivar 'BRXSI13-0' produce foliage that is entirely silver colored on the upper surface, whereas the seed parent produces silver and pink colored foliage. Additionally, plants of the new variety produce twice as many new branches from a pinch, and grower faster and bushier than the seed parent.

Plants of the new cultivar 'BRXSI13-0' are similar to plants of the pollen parent variety, in most horticultural characteristics. However, plants of the new cultivar 'BRXSI13-0' produce foliage that is smaller than the pollen parent. Additional differences include a faster plant growth by 'BRXSI13-0', although plants of the new variety also resist stretching under warm, humid conditions. Plants of the new variety also produce more compact petioles, than the pollen parent.

COMMERCIAL COMPARISON

Plants of the new cultivar 'BRXSI13-0' are similar to plants of the unpatented commercial variety, *Begonia rex cultorum* 'Fairy' in most horticultural characteristics. However, plants of the new cultivar 'BRXSI13-0' produce smaller, more abundant leaves on a fuller, bushier plant. Additionally 'BRXSI13-0' is faster growing and continues to grow more consistently during the colder winter months than 'Fairy'. Additionally the new variety has much stronger basal branching than 'Fairy'.

Plants of the new cultivar 'BRXSI13-0' are similar to plants of the unpatented commercial variety, *Begonia rex cultorum* 'Lalome' in most horticultural characteristics. However, plants of the new cultivar 'BRXSI13-0' grow faster, under colder temperatures. conditions. Additionally the new variety produces foliage resistant to pink coloration under lower temperatures, and plants that have stronger basal branching than 'Lalome'.

BRIEF DESCRIPTION OF THE PHOTOGRAPH

The accompanying photograph in FIG. 1 illustrates in full color a typical plant of 'BRXSI13-0' grown in a greenhouse. The pot size is a commercial 6 inch pot. The plant shown is approximately 6 months old.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'BRXSI13-0' plants grown in a commercial controlled greenhouse in Oxnard, Calif. Temperatures ranged from 15° C. to 28° C. during the day and 18° C. to 22° C. at night. No artificial light, photoperiodic treatments or chemical treatments were given to the plants. Measurements and numerical values represent averages of typical plant types.

Botanical classification: *Begonia rex cultorum* 'BRXSI13-0'.
Age of plant described: Approximately 8 months.
Container size of plant described: 6 inch pot.

PROPAGATION

Type of propagation typically used: Vegetative leaf cuttings.
Time to roots: About 25 days at approximately 20° C.
Root description: Dense and fibrous.

PLANT

Growth habit: Upright growing, outwardly arched fleshy annual.
Pot size of plant described: 6 inch.
Height: Approximately 40 cm.
Plant spread: Approximately 59 cm.
Growth rate: Rapid.
Branching characteristics: Mainly basally emerging foliage. Branching can occur on oldest petioles, with 2 or 3 petioles emerging in different locations along these mature petioles.
Length of lateral branches: Average 8 cm.
Quantity of lateral branches: Approximately 4 to 6 on an 8 month old plant.
Characteristics of lateral branches:
- *Diameter.*—Approximately 0.5 cm.
- *Color.*—Near RHS Greyed-Purple 184B.
- *Texture.*—Pilose, hairs approximately 0.1 cm to 0.2 cm, colored near White N155B.
- *Strength.*—Flexible, very strong.

Internode length: Average 2.0 cm to 4.0 cm.

FOLIAGE

- *Type.*—Single, basally emerging foliage and long petioles.
- *Orientation.*—Outwardly or upwardly facing foliage. Attachment approximately 75 degree angle to petiole.
- *Strength.*—Very strong, and flexible, resists breakage.
- *Texture, top surface.*—Rugulose, mainly non-pubescent. Hispidlike hairs, found throughout blade, approximately 0.5 cm apart. Approximately 0.1 cm in length, colored near Greyed-Green 188D.
- *Texture lower surface.*—Rugose, main surface non-pubescent, veins mildly hispid. Hairs approximately 0.1 cm long, colored near RHS White 155C.
- *Appearance.*—Very shiny, irredescent upper surface. Under surface matte.
- *Quantity.*—Approximately 18 fully expanded mature leaves and approximately 20 immature leaves.
- *Shape of blade.*—Reniform.
- *Apex.*—Cirrose.
- *Base.*—Cordate, asymmetrical.
- *Margin.*—Deeply dentate, with additional serrations.
- *Aspect.*—Recurved.

Mature leaves:
- *Average length.*—Approximately 19 cm.
- *Average width.*—Approximately 15 cm.
- *Color.*—Mature foliage upper side: Main blade near Greyed-Green 188C. Margin and blotch near petiole attachment, near Greyed-Green N189A. Mature foliage under side: Background color near Greyed-Green 191A, almost completely covered with flush near Greyed-Purple 187B. Completely colored Greyed-Purple 187B near petiole attachment and margin.
- *Venation.*—Type: Palmate. Venation color upper side: Near RHS Greyed-Red 179C, at petiole attachment. Mid section of blade veins are near Greyed-Green 188C with slight Purple 68A tint. Venation color under side: Near RHS Greyed-Purple 187B.

Immature leaves:
- *Average length.*—Approximately 12 cm.
- *Average width.*—Approximately 8 cm.
- *Color.*—Immature foliage upper side: Main blade near Greyed-Green 188C. Margin and blotch near petiole attachment, near Greyed-Green N189A. Less dark blotching than mature leaves. Faint flush along veins near Red-Purple 64A. Immature foliage under side: Near RHS Greyed-Green 191A. Veins, margin and blotch near petiole near Greyed-Purple 187A.

Venation:
- *Type.*—Palmate.
- *Venation color upper side.*—Near RHS Greyed-Green 191A.
- *Venation color under side.*—Near RHS Greyed-Purple 186B.

Petiole:
- *Length.*—Average Range Approximately 13 to 22 cm.
- *Diameter.*—Approximately 0.8 cm.
- *Color.*—Near RHS Greyed-Red 178B.
- *Texture.*—Pilose. Hairs range from approximately 0.1 cm to 0.3 cm long, colored near RHS White N155C.

Stipule description: Stipules infrequently present, in 1 or 2 per petiole. Drying and falling off as leaves mature.
- *Length.*—Approximately 1 cm. Length includes 0.2 cm awn.
- *Diameter.*—Approximately 0.8 cm.
- *Apex.*—Aristate.
- *Base.*—Truncate.
- *Color.*—Near RHS Greyed-Red 182A, upper and lower. Transparent appearance.
- *Texture.*—Upper Surface: Glabrous. Lower Surface: Slightly pilose.

FLOWER

Flowering habit: Flowering not observed.

OTHER CHARACTERISTICS

Seeds and fruits: Not Observed.
Disease/pest resistance: Neither resistance nor susceptibility to diseases or pests of *Begonia* has been observed in this variety.
Temperature tolerance: The new variety tolerates temperatures from approximately 0° C. to 35° C.

What is claimed is:

1. A new and distinct cultivar of *Begonia* plant named 'BRXSI13-0' as herein illustrated and described.

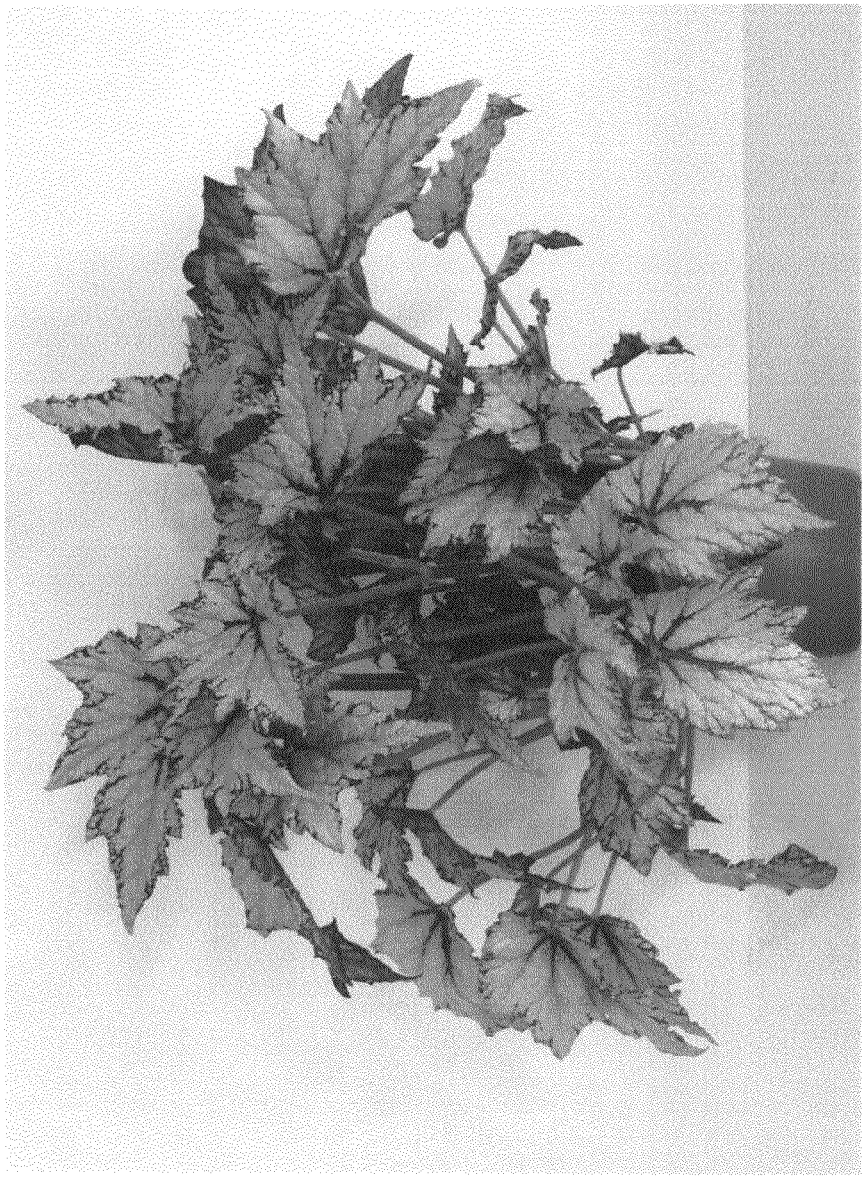

* * * * *